United States Patent [19]
Lapeyre et al.

[11] Patent Number: 6,068,657
[45] Date of Patent: May 30, 2000

[54] MECHANICAL VALVE PROSTHESIS WITH OPTIMIZED CLOSING MODE

[76] Inventors: Didier Lapeyre, 7120 Chaignes, Pacy Sur Eure; Philippe Perrier, 4 rue Alphonse Daudet, 78860 St-Nom-La-Breteche, both of France

[21] Appl. No.: 09/035,981

[22] Filed: Mar. 6, 1998

Related U.S. Application Data

[63] Continuation of application No. 08/859,530, May 20, 1997.
[51] Int. Cl.$^7$ ........................................... A61F 2/24
[52] U.S. Cl. .................................................. 623/2
[58] Field of Search ............................ 623/2, 11, 900

[56] References Cited

U.S. PATENT DOCUMENTS

| | | |
|---|---|---|
| 4,120,299 | 10/1978 | Russo . |
| 4,676,789 | 6/1987 | Sorensen et al. . |
| 4,808,180 | 2/1989 | Johnson . |
| 4,820,299 | 4/1989 | Philippe et al. . |
| 4,872,875 | 10/1989 | Hwang . |
| 5,026,391 | 6/1991 | McQueen et al. . |
| 5,080,669 | 1/1992 | Tascon et al. ............................... 623/2 |
| 5,116,367 | 5/1992 | Hwang et al. ............................... 623/2 |
| 5,123,918 | 6/1992 | Perrier et al. ............................... 623/2 |
| 5,207,707 | 5/1993 | Gourley ....................................... 623/2 |
| 5,314,467 | 5/1994 | Shu ............................................ 623/2 |
| 5,843,183 | 12/1998 | Bokros et al. ............................... 623/2 |

FOREIGN PATENT DOCUMENTS

| | | | |
|---|---|---|---|
| 092002197 | 2/1992 | WIPO ....................................... 623/2 |
| 093017637 | 9/1993 | WIPO ....................................... 623/2 |

OTHER PUBLICATIONS

C. Peskin et al., "The aortic sinus vortex", Federation Proceedings, Dec. 1978, vol. 37, No. 14, pp. 2784–2792.

M. Jones et al., "Doppler Color Flow Evaluation of Prosthetic Mitral Valves: Experimental Epicardial Studies", Journal of the American College of Cardiology, Jan. 1989, vol. 13, No. 1, pp. 234–240.

K. Dellsperger et al., "Regurgitation of Prosthetic Heart Valves: Dependence on Heart Rate and Cardiac Output", The American Journal of Cardiology, Jan. 15, 1983, pp. 321–328.

Y. Kiyota et al., "In vitro closing behavior of the St. Jude Medical heart valve in the pulmonary position," The Journal of Thoracic and Cardiovascular Surgery, Sep. 1992, vol. 104, No. 3, pp. 779–785.

R. T. Johnston et al., "Carbomedics and St. Jude Medical bileaflet valves: an in vitro and in vivo comparison", European Journal of Cariothoracic Surgery, vol. 6, No. 4, 1992, pp. 267–271.

J. T. Baldwin et al., "Mean Velocities and Reynolds Stresses Within Regurgitant Jets Produced by Tilting Disc Valves", ASAIO Transactions, Jul.–Sep. 1991, vol. 37, No. 3, ISSN 0889–7190, pp. M348–M349.

(List continued on next page.)

*Primary Examiner*—Jeffrey A. Smith
*Assistant Examiner*—Eduardo C. Robert
*Attorney, Agent, or Firm*—Morgan, Lewis & Bockius LLP

[57] ABSTRACT

The invention relates to a mechanical valve prosthesis that includes a base having an external portion forming a suture ring, and an internal portion forming a rim, in which a blood flow can move in a main flow direction (F), as well as at least two closing leaflets (10) which can move, under the action of the blood flow, between a closed position and an open position, and vice versa. The opening occurs in the physiological direction, that is from the axis of the rim (3) of the center of the prosthesis and thus toward the rim. A region (40) of each one of the leaflets (10) borders, in the open position, a natural wall and defines with it the peripheral duct regions (19). The region (40) of each leaflet (10) presents a zone (22) in which, in the closed position, it turns its concavity toward the rim (3). In this manner, when the leaflet (10) is in the open position, the peripheral duct regions (19) present a form which produces a beginning of closing of the valve (10) during the deceleration of the blood flow.

15 Claims, 6 Drawing Sheets

OTHER PUBLICATIONS

J. Skoularigis et al., "Frequency and Severity of Intravascular Hemolysis After Left–Sided Cardiac Valve Replacement with Medtronic Hall and St. Jude Medical Prostheses, and Influence of Prosthetic Type, Position, Size and Number", The American Journal of Cardiology, Mar. 1, 1993, pp. 587–591.

H. Baumgartner et al., "Color Doppler Regurgitant Characteristics of Normal Mechanical Mitral Valve Prostheses In Vitro", Circulation, vol. 85, No. 1, Jan. 1992, pp. 323–332.

R. Koppensteiner et al., "Blood Rheology After Cardiac Valve Replacement with Mechanical Prostheses or Bioprostheses", The American Journal of Cardiology, Jan. 1, 1991, pp. 79–83.

T. C. Lamson et al., "Relative Blood Damage in the Three Phases of a Prosthetic Heart Valve Flow Cycle", ASAIO Journal, Jul.–Sep. 1993, vol. 39—No. 3, ISSN 1–58–2916, pp. M626–M633.

MECHANICAL VALVE PROSTHESIS WITH OPTIMIZED CLOSING MODE

This is a continuation of copending application Ser. No. 08/859,530 filed on May 20, 1997, which is hereby incorporated by reference.

BACKGROUND OF THE INVENTION

1. Field of Invention

The invention relates to a mechanical valve prosthesis having at least two leaflets.

2. Description of Related Art

The designers of valve prostheses devices have, until now, focused design efforts essentially on the opening mechanism of the leaflets. However, the closing mechanism of natural cardiac valves is a subject little known to surgeons, and it is still neglected by most of the designers of mechanical valve prostheses. It has for a long time intrigued physiologists and specialists in fluid mechanics. Today, there is agreement in recognizing that the aortic sinuses and the ventricular cavity constitute "pressure stablilization chambers" (the output regimen of the two coronary arteries is diastolic and not systolic: thus, they do not empty during the contraction of the heart) the posterior (downstream) side of the leaflets which promote, during the flow of the blood, the formation of a very slight pressure gradient between these cavities and the opposite (upstream) side of the leaflets. Due to this anatomical arrangement, the pressure exerted on the leaflets during blood flow is not identical at a given time on the anterior (upstream) sides and the posterior (downstream) sides. There is a slight delay, or hysteresis, which generates a transient moment of force which induces an early and progressive movement of closing as soon as the acceleration of the flow decreases. This phenomenon is thus connected:

(1) with the pulsed nature of the output; and
(2) the geometric configuration of the natural valve system.

Studying the human aortic device, Leonardo da Vinci, as early as 1514, had a brilliant intuition about this unusual hydrodynamic phenomenon: "It is the same force which opens the valve and which closes it." We therefore have suggested calling this phenomenon the "Leonardo da Vinci effect."

In the early 1980s, A. A. Van Steenhoven confirmed, by direct in vitro high-speed cinematography, that, during pulsed output, the natural aortic valves move gradually to the center of the valve during the deceleration of the output, so that a very small reflux is required to complete the closing. The beginning of the closing starts during the deceleration phase, and 60–80% of the closing is completed before the aortic flow becomes zero.

Charles Peskin also studied this phenomenon by mathematical modeling of lows ("The aortic sinus vortex": Mathematical modeling and computation in physiology. The American Physiological Society. Federation Proceedings, Vol. 37, No.14, December, 1978). He concluded that the closing of the aortic valve is virtually synchronous with the time when the flow becomes zero (Ann Rev Fluid Mech 1982, Vol. 14, pp. 235–269).

Mano J. Thubrikar, in a very detailed radiography study of the movement of aortic valves equipped with radioopaque markers confirmed this phenomenon in 1993 in animals:

"The aortic valve rapidly opens until a maximum opening size is obtained, and then, it closes slowly, but partially, during most of the systole, and finally, it rapidly and completely closes" (High-speed cine-radiographic study of aortic valve leaflet motion. The Journal of Heart Valve Diseases. Vol. 2, No.6, November 1993).

In the mitral position, the ventricular cavity creates an anatomical arrangement comparable to that of the sinuses. This geometry thus also promotes the closing of the leaflets before the reversal of the flow. It has been confirmed by echo-Doppler studies in humans that the natural valve, in contrast to mechanical prosthetic valves, closes before the start of the ventricular contraction:

"At the end of diastole, the blood displaced toward the left ventricle appears with a reversal of direction along the free wall of the left ventricle and the septum, closure closing of the mitral valve leaflets before the onset of the left ventricle mechanical systole. Because of this event [. . .], the mitral valve closed with a minimal closure volume, having a duration of no more than 10–20 msec (Michael Jones et al., Doppler color flow evaluation of prosthetic mitral valve: Experimental epicardial studies. Journal of the American College of Cardiology, Vol. 13, No. 1, January, 1989, pp. 234–240).

This natural closing mechanism eliminates the hydraulic "bumps" at the time of the closing. The closing is progressive and gentle. The mechanical stresses exerted on the structures are small, and the lifespan of the natural valve is much longer than that of the prosthesis. Function thus created the optimal shape. It is interesting to note that in the entire venous systems, notably in the lower limbs, the same sinusal dilations can be found around numerous antireflux valves.

To this day, the designers of cardiac valves have focused their efforts primarily on the reduction of losses of charge and of shearing forces during the direct flow (forward flow). They have neglected the closing phase and the trauma caused to the blood by the reversed flow or reflux (backward flow).

The natural closing mechanism of cardiac valves has not been taken into account until today in the design of mechanical valve prosthesis, i.e., at the end of the ejection deceleration, at the time when the flow rate becomes zero, if the natural aortic valve is already more than 90% closed, in contrast, all the known mechanical valve prostheses at that instant remain at least 90% open. From this clearly open position, these valves very abruptly close with the reflux, in an aortic position at the very beginning of the diastole, and in the mitral position, even more abruptly at the very beginning of the systole (<10 msec). The mean angular speed of closing at the physiological frequency of 70 cycles per minute is on the order of 1.2–1.5 m/sec, whereas it is at the most 60 cm/sec with the natural valves.

Cardiac valve specialists only recently have become interested in the closing phase, because of its incidences on the phenomena of cavitation, which can cause damages to the components and result in a safety risk. Most work on this subject has, thus, been performed after the design of the mechanical valves which are on the market today.

"Until now, the influence of the valve closing phase on the damage caused to the blood has been considered to be small compared to that of the opening phase and that of losses of charge in the flow from upstream to downstream. In this perspective, it is necessary to take into account the fact that an early and rapid closing of the valve is associated with small regurgitation rates, which in turn minimizes the angular closing speeds and the impacts" (H. Reul et al., Surgery for heart valve diseases. Published by ICR Publishers, Londres, 1990, Endre Bodnar, Editor).

The conventional mechanical valve prostheses devices, thus, present several drawbacks, including:

1. Existence of a dynamic closure volume on the order of 4% of the ejected blood volume in the aortic position and 8% of the ejected blood volume in the mitral position, which decreases the yield of the valve and increases the work of the heart.

2. A rapid angular closing speed at the origin of cavitation phenomena. This high speed increases the intensity of the impact at closing and it generates sufficiently large acoustical vibrations to cause discomfort to the patients.

3. Severe dysfunction at low flow rate and high frequency: for cardiac flows of less than 3 L/min, which are naturally accompanied by a reactive acceleration of the cardiac rhythm greater than 110 cycles per minute, the closure volume increases in a semilogarithmic manner, and the ejection fraction can exceed 80% of the systolic volume. Under these conditions, a true state of acute cardiac insufficiency can occur, because the heart becomes incapable of ensuring a sufficient output to maintain life.

This functional insufficiency was already reported in 1983 (Kevin C. Dellsperger, Regurgitation of prosthetic heart valves. The American Journal of Cardiology, January 15, 1983, Vol. 51):

"All the cardiac valves have total regurgitation fractions greater than 20% once cardiac output is less than 4 L/min and the heart rate is greater than 110 bpm. At rates equivalent to clinical tachycardia, closure backflow is the major component of the regurgitation, while the leakage [back]flow is the major component of the regurgitation at rates equivalent to clinical bradycardia.

"For a patient with tachycardia and low cardiac output, backflow may present an enormous demand on the cardiac energy supply. [. . .] In this case, the systemic elevation of the pressure rather tends to worsen the situation than improve it. [. . .] Consequently, a valve which has a low closure backflow would be the hemodynamically favorable [. . .].

"The performances of the mechanical valves are poorly adapted insofar as regurgitation in concerned, as soon as the output is less than 2 L/min. There is a semilogarithmic relation between the increase in the flow and the performance of a valve. The total regurgitation increases very rapidly when the cardiac output. Under routine clinical conditions of low cardiac flow and arrhythmia, the thrombogenicity of the valves is very quickly exacerbated [. . .].

"Therefore, it is imperative that the prosthetic valves in the future be designed to minimize regurgitation."

Curiously, this functional anomaly is little known to cardiologists and surgeons, and it has been studied in depth only since 1993 (Endré Bodnar and H. Reul. Prosthetic valve function under simulated low cardiac output conditions. The Journal of Heart Valve Disease, Vol. 2, No. 3, May, 1993). The in vitro studies have shown that cardiac valves of natural origin (homografts and bioprostheses) do not present this anomaly, whose consequences can be very severe on patients having mechanical valve prostheses.

The transient episodes of tachyarrythmia with low output are in fact observed relatively frequently in human clinical medicine. They occur when the cardiac function is altered, which is not rare in patients who are candidates for a valve replacement.

They are also frequent if the patient suffers from bleeding, even if minimal, at the end of the intervention, which is not rare.

Under these circumstances, the major functional valve insufficiently is often not recognized by anesthesiologists and surgeons, and it can lead to death, because the heart is unable to resume an effective function.

The catastrophic consequences of this functional insufficiency are even more frequent in patients who have two mechanical valves (aortic and mitral).

Finally, it has been demonstrated that this functional anomaly makes valve prostheses with two leaflets incompatible with the low-pressure regimen in the right cavities of the heart (Yoshiharu Kiyotta et al., In vitro closing behavior of the St. Jude Medical heart valve in the pulmonary position. The Journal of Thoracic and Cardiovascular Surgery, Vol. 104, No. 3, September, 1992).

The severe leakage which accompanies the episodes of tachyarrythmia and low output maintains and worsens the increase in the [heart] rate and it can, in some cases, induce a vicious circle with a rapidly fatal outcome. It is true that sudden deaths are observed in all patients with altered cardiac function, whether or not they have valve prostheses. (In these cases, it is precisely rhythm disorders that are incriminated). The number of unexplained and unexpected sudden deaths is, however, particularly high (approximately 15% over 10 years) in patients who have mechanical valves. The mechanism has remained mysterious to this day. The considerable valve leakage, when the output is low, and the high heart rate today appear to be a promoting factor.

4. Need for a very precise control of the seal:

An inevitable static leakage is added to the dynamic closure volume in all mechanical valves, because it is not possible to obtain a perfect seal with rigid materials. This static leakage ("gap flow") occurs through a space of a few hundreds of millimeters between the closing elements and the opening of the valve.

In the mitral position, for a period corresponding to one cardiac cycle, the dynamic closure volume is two times greater than the static leakage, because the mitral sizes are greater than the aortic sizes. In the aortic position, for a period corresponding to one cardiac cycle, the static leakage volume is two times greater than the dynamic closure volume (although the leakage occurs at a lower pressure than in the mitral position, its duration is in fact longer: 450 msec versus 300 msec). This considerable static leakage in the aortic position is even more noteworthy given that the sizes of the valves are smaller.

The static and dynamic leakage volumes of the cardiac valves most routinely used today throughout the world are the following: (R. T. Johston: European Journal of Cardiothoracic Surgery, 1992, Vol. 2: pp. 267–271).

| 1/ REGURGITATION EN POSITION MITRALE: Valve 29 de Carbomedics (CM) contre Valve 29 de St-JUDE MEDICAL (SJM) (saline, pression aortique = 120/80 mm Hg) | | | | | | | |
|---|---|---|---|---|---|---|---|
| Rhythme cardiaque 2/ | Volume expulsé 3/ | Débit cardiaque 4/ | CM volume de fermeture 5/ | CM fuite statique 6/ | SJM volume de fermeture 7/ | SJM fuite statique 8/ |
| 72/mn | 70 ml | 4.5 1/mn | 5.0 ml | 2.0 ml | 5.5 ml | 2.9 ml |
| 120/mn | 80 ml | 9.0 1/mn | 6.0 ml | 1.9 ml | 16.5 ml | 1.8 ml |

Key:
1 REGURGITATION IN MITRAL POSITION: Carbomedics (CM) valve 29 versus St. Jude Medical (SJM) valve 29 (saline, aortic pressure = 120/80 mm Hg)
2 Heart rate
3 Expelled volume
4 Cardiac output
5 CM closure volumes
6 CM static leakage
7 SJM closure volume
8 SJM static leakage

| 1/ REGURGITATION EN POSITION AORTIQUE: Valve 23 de Carbomedics (CM) contre Valve 23 de St-JUDE MEDICAL (SJM) (saline, pression aortique = 120/80 mm Hg) | | | | | | | |
|---|---|---|---|---|---|---|---|
| Rhythme cardiaque 2/ | Volume expulsé 3/ | Débit cardiaque 4/ | CM volume de fermeture 5/ | CM fuite statique 6/ | SJM volume de fermeture 7/ | SJM fuite statique 8/ |
| 72/mn | 70 ml | 4.5 1/mn | 1.5 ml | 4.9 ml | 2.8 ml | 5.0 ml |
| 120/mn | 80 ml | 9.0 1/mn | 1.8 ml | 2.6 ml | 3.0 ml | 4.3 ml |

Key:
1 REGURGITATION IN AORTIC POSITION: Carbomedics (CM) valve 23 versus St. Jude Medical (SJM) valve 23 (saline, aortic pressure = 120/80 mm Hg)
2 Heart rate
3 Expelled volume
4 Cardiac output
5 CM closure volumes
6 CM static leakage
7 SJM closure volume
8 SJM static leakage The total regurgitation volume corresponding to the resting heart rate and cardiac output values in humans is thus between 10 and 14% of the volume of blood ejected at each cycle with bileaflet valves. The existence of a large dynamic closure volume thus requires controlling the static leakage by reducing as much as possible the gap between the components. This need requires over high degree of precision in the manufacturing of the components and the high cost. In practice, to maintain a total leakage output at a tolerable level, the value of the interstice between the components must not exceed 4–5/100 mm.

Although the mechanical valve prostheses have been used for 30 years, the biological and medical consequences of the static leakage have only recently been demonstrated: the passage of a small volume of blood under pressure at each cycle through this very narrow interstice is very traumatic for the blood cells.

It is easier to understand the biological consequences if the leakage is considered over a whole day, not only one single cardiac cycle: in a man with a mitral valve of the St. Jude type, size 29 [mm], approximately 300 L of blood pass each day through a 3/100 to 5/100-mm slit at a pressure with pulses from 0 to 160 mm Hg. In the case of an aortic St. Jude valve of size 23 mm, the static leakage is more than 500 L per day at a constant pressure of 80 mm Hg (Rosenberg et al., Relative blood damage in the three phases of a prosthetic heart valve flow cycle. Journal of the American Society for Artificial Internal Organ, 1993). With regard to the corresponding dynamic closure volume, it is on the order of 500 L/day in the mitral position and 300 L/day in the aortic position. The total leakage flow is thus on the order of 800 L/day in both cases.

Today, it is assumed that the thrombogenicity of cardiac valves is primarily due to turbulences which occur during the flow from upstream to downstream and to the resulting activation of the coagulation mechanisms. Engineers have therefore primarily focused on load losses and the Reynolds turbulence stresses during the direct flow (forward flow). The critical threshold for injury which the biologists use is 1500 dyne/cm$^2$ for the red blood cells and 100 dyne/cm$^2$ for the platelets. This threshold is always exceeded (1000–3000 dyne/cm$^2$) during this main phase of the flow for a large variety of mechanical cardiac valves.

Destruction of red cells and platelets is indeed observed in all patients having mechanical valves. The lifespan of red blood cells is reduced by nearly half. The same applies to platelets. This destruction is greater in the mitral position than the aortic position. It causes a compensatory increase in fibrinogen production by the liver and biological reactions which create a latent state of hypercoagulability which was recently identified. It is therefore not very surprising, under these conditions, that the patients have a need for anticoagulants. It is true that the destruction of blood cells is not sufficiently extensive in most cases to cause clinical signs, given that the bone marrow compensates for this destruction by increasing its production. However, it is sufficiently severe to cause an anemia identified in 3–15% of the patients and it causes biological modifications in all patients.

Although the reverse flow or reflux (backward flow) is quantitatively 25 times lower than the direct flow (forward flow) (approximately 7000 L/day), it is important to emphasize that the critical threshold for injury to red blood cells and platelets is exceeded by much more during backward flow than forward flow. Baldwin et al. have measured a value of 20,000 dyne/cm$^2$ through a monodisk Bjork-Shiley valve of size 27 mm (Mean velocities and Reynold stresses within regurgitant jets produced by tilting disc valves: ASAIO Trans, Vol. 37, pp. M348–349, 1991). When the valve is in the closed position, the higher the pressure gradient across the leaflets is, the greater the shearing rate of the blood and the greater the degree of hemolysis. The cell trauma during the leakage phase is therefore not negligible.

It has been shown in patients that there is no relation between the valve size and the degree of hemolysis. These recent observations tend to demonstrate that the shearing during the flow phase is not preponderant in cell destruction. In contrast, although the static leakage is much less in the mitral position than in the aortic position, the destruction of the red blood cells is much greater with the mitral valves (see John Skoularigis et al.: Frequency and severity of intravascular hemolysis after left-sided cardiac valve replacement with Medtronic-Hall and St. Jude medical prostheses, and influence of prosthetic type, position, size and number. The American Journal of Cardiology, Vol. 71, March 1, 1993). This can only be explained by the fact that the leak through the gap takes place in the mitral position under a very different pressure and speed regimen.

The shearing rate also depends on the gap width. For equal sizes, St. Jude valves provide a better seal than the Medtronic-Hall valves. The mean leakage outputs are respectively on the order of 8 cm³/sec and 13 cm³/sec. Comparative studies of the hemolysis rate, however, show a greater hemolysis in patients having St. Jude medical valves than patients having Medtronic-Hall valves (see Baumgartner et al.: Circulation, Vol. 85, No. 1, January, 1992 and Taggart, D. P. et al.: Severe haemolysis with the St. Jude Medical prosthesis. European Journal of Cardiovascular Surgery, 1988; Vol. 2, pp. 137–142).

SUMMARY OF THE INVENTION

The object of the present invention is a valvular prosthesis presenting at least two leaflets made of rigid materials which open in the physiological direction (i.e., direction of blood flow), which prosthesis presents an improved dynamic function and notably overcomes at least partially the first three drawbacks described above.

The basic idea is to adapt the profiles of the leaflets of the valve by creating a zone in which the leaflet in the open position turns its concavity towards the rim of the prosthesis, this zone being located, after the prosthesis has been implanted in the patient, in the vicinity of a natural wall, that is, in the aortic position, in the vicinity of the aortic sinus, and, in the mitral position, in the vicinity of the wall of the left ventricle, delimiting peripheral duct regions. The shape of these duct regions can induce the beginning of opening of the valve during the flow deceleration, in such a manner that a notable closing percentage is obtained before the reversal of the blood flow, resulting in a decrease in the volume regurgitated during the closing.

The invention thus provides a mechanical valve prosthesis having a base with an external portion which forms a suture ring, and an internal portion which forms a rim in which blood flow can move in a main flow direction parallel to the axis of the rim, and at least two closing leaflets which can move, under the action of the blood flow, between a closed position and an open position, and vice versa. Each one of the leaflets has a tilt axis presetting a leading edge which is in contact, except for the gap, with the rim in the closed position and which is located upstream from the flow in the open position, and a trailing edge in contact, except for the gap, with the trailing edge of the other leaflet(s) in the closed position and which is located in the downstream direction of the flow in the open position. The opening of the axis of the rim thus occurs towards the rim, each one of the leaflets has a region which extends between the leading edge and the trailing edge and which borders, in the open position, the rim as well as a natural wall when the valve is implanted in a patient, and defines with the rim and the wall, peripheral duct regions. This region of each leaflet presents a zone in which, in the open position, it turns its concavity towards the rim, and thus towards said wall.

The most likely hypothesis is that the improvement in the dynamic function of the prosthesis is obtained because of the fact that these zones which have a concavity turned towards the rim allow the exploitation of the movements of the blood flow in the sinus cavities at the time of the deceleration of the blood flow, which are wall currents directed from downstream to upstream and thus countercurrent with respect to the blood flow, to generate an instantaneous excess pressure on the downstream side of the leaflets, which promotes their closing.

The prosthesis according to the invention also provides that, in the open position, the region of each leaflet presents, in a cross section through a section plane containing, on the one hand, the axis of the rim and, on the other hand, the tip of the leaflet closest to the axis of the rim, a profile having a maximum curvature directed towards the axis of the rim that is between 1% and 20% of the length L of the leaflet that is defined as the distance between the leading edge and the trailing edge, taken in a cross section of the leaflet in the open position.

For each leaflet in the open position, a straight line joining the ends of the [cross] section of the leaflet through said first plane forms, with the axis of the rim, an angle between −10° and +10°. In the case of symmetrical leaflets, the first plane as defined above is the plane of symmetry of the corresponding leaflet.

The prosthesis has at least one of the first and second maximum curvatures between 5% and 15%. At least one of the first and second maximum curvatures can be between 10% and 15%, and preferably between 5% and 10%.

Satisfactory results can be obtained by changing the profile of the leaflets a little in comparison to a flat shape when at least one of the first and second maximum curvatures is between 1% and 5% and, more particularly, between 3% and 5%.

According to one preferred embodiment, the present invention provides a mechanical valve prosthesis with leaflets made of rigid material that also overcomes, at least partially, the fourth above-mentioned drawback.

According to a first variant of this preferred embodiment, which is particularly well suited for a mitral valve, the man value of the interstice between the leading edge of the leaflets and the rim and/or the interstice between the trailing edges is, in the closed position, between 40 and 100 µm and preferably between 60 and 90 µm. An interstice having as large a mean value is functionally acceptable to the extent that the regurgitated volume during the closing has been decreased, and as a result the total leakage volume remains acceptable. The increase in the mean value of the interstice has the effect of increasing the output and thus the effectiveness of the "rinsing jets" and the effect of decreasing the shearing to which the red blood cells and the platelets are subjected and thus the hemolysis. Although there is still no scientifically proven relation between the degree of the hemolysis and the thrombogenicity of the cardiac valves, clinical experience suggests that the reduction in the shearing forces can decrease the thromboembolic complications by reducing the state of reactive hypercoagulability which accompanies any globular destruction (Renate Koppensteiner et al.: Blood rheology after cardiac replacement with mechanical prostheses or bioprostheses. The American Journal of Cardiology, January 1, 1991, pp. 79–83): tissue valves, which are known to have low thrombogenicity, do not cause any hemolysis; the mitral prostheses are known to be more thrombogenic than the aortic prostheses.

According to the invention, it is advantageous for each one of the leaflets to present a tilt axis located at a distance at least equal to 75% of the value of the internal radius, this distance being preferably between 80% and 85% of the value of said radius.

Other characteristics and advantages of the invention will become more apparent after a reading of the following description, which is given as a nonlimiting example, with reference to the drawings.

BRIEF DESCRIPTION OF THE DRAWINGS

The invention is described in relation to the following drawings, wherein.

DETAILED DESCRIPTION OF PREFERRED EMBODIMENTS

The valve prosthesis includes a base 1 comprising an external part 2 forming a suture ring, and an internal part 3 forming a rim in which blood can move from upstream to downstream in the direction of the arrow F. Closing leaflets 10, in this case 3, open under the action of the pulsed blood flow in the direction of the arrow F from a nominal closed position (FIG. 2) to a nominal open position (FIGS. 1a and 1b) in which the leaflets 10 are in abutment with the rim 3. Each one of the leaflets 10 opens in the physiological direction about the tilt axis 11, and its central region 40 presents a leading edge 12 which, in the closed position, is in contact with the rim 3 along a contour 14 (represented in dotted line in FIG. 2), and a trailing edge 16 which is in contact with the trailing edge 16 of the other leaflets 10. Each trailing edge 16 presents, in the case of a prosthesis with more than two leaflets, a distal point C located in the extreme downstream part of the leaflet.

The central region 40 of each one of the leaflets 10 presents an anterior side 17 directed towards the upstream region when the leaflets are closed, and a posterior side 18 directed towards the downstream region when the leaflets 10 are closed. In the open position of the valve, the downstream side 18 of each leaflet 10 borders the rim 3, and as a result, once the valve has been placed in a patient, the downstream side 18 of each leaflet 10 also borders a natural wall 20 (wall of the aortic sinus, or of the cavity of the left ventricle) and it forms with the rim 3 and the wall 20 a peripheral duct zone 19 which forms as many narrow passages with respect to the central flow duct delimited by the sides 17.

Inside the rim 3, the lateral edges 30 prolong, on each side, the central region 40 of each one of the leaflets 10 and they present a contour 15 which extends the contour 14 of the leading edge proper 12 and a contour 31 which extends the trailing edge proper, 16. The lateral edges 30 thus constitute transitional profiles between the leading edge 12 and the trailing edge 16. In the closed position, the contour 15 of the lateral edges 30 is in contact with the rim 3 and the contours 31 of the lateral edges 30 of the adjacent leaflets 10 come in contact with each other. By definition, the leading edge proper, 12, is considered to be delimited by the contour 14 of the central region 40 of the leaflet 10, and the trailing edge proper is delimited at the edge 16 of the central region 40.

In the standard case, a prosthetic valve closes essentially due to the action of the reverse blood flow or reflux in the opposite direction of the arrow F, resulting in a regurgitated closure volume which is not negligible and which can be a very large fraction of the blood flow in the case of a low cardiac output and tachycardia. Since the closure volume is constant, the regurgitated volume per unit of time is proportional to the cardiac rhythm. If, in addition, the cardiac output is low, the closure volume rapidly becomes a large fraction of the ejected volume. The invention allows decreasing the closure volume by adapting the profile of the downstream side 18 of the region 40 in such a manner that it presents a zone 22 which turns its concavity towards the rim 3 and thus toward the wall 20, which allows the exploitation of the movements of the blood flow to generate an instantaneous excess pressure on the downstream side 18 of the leaflets at the time of the deceleration of the blood flow. In the example represented in FIGS. 1–4, the zone 22 extends over a major part of the length L of the corresponding leaflet 10.

Figure 1A:
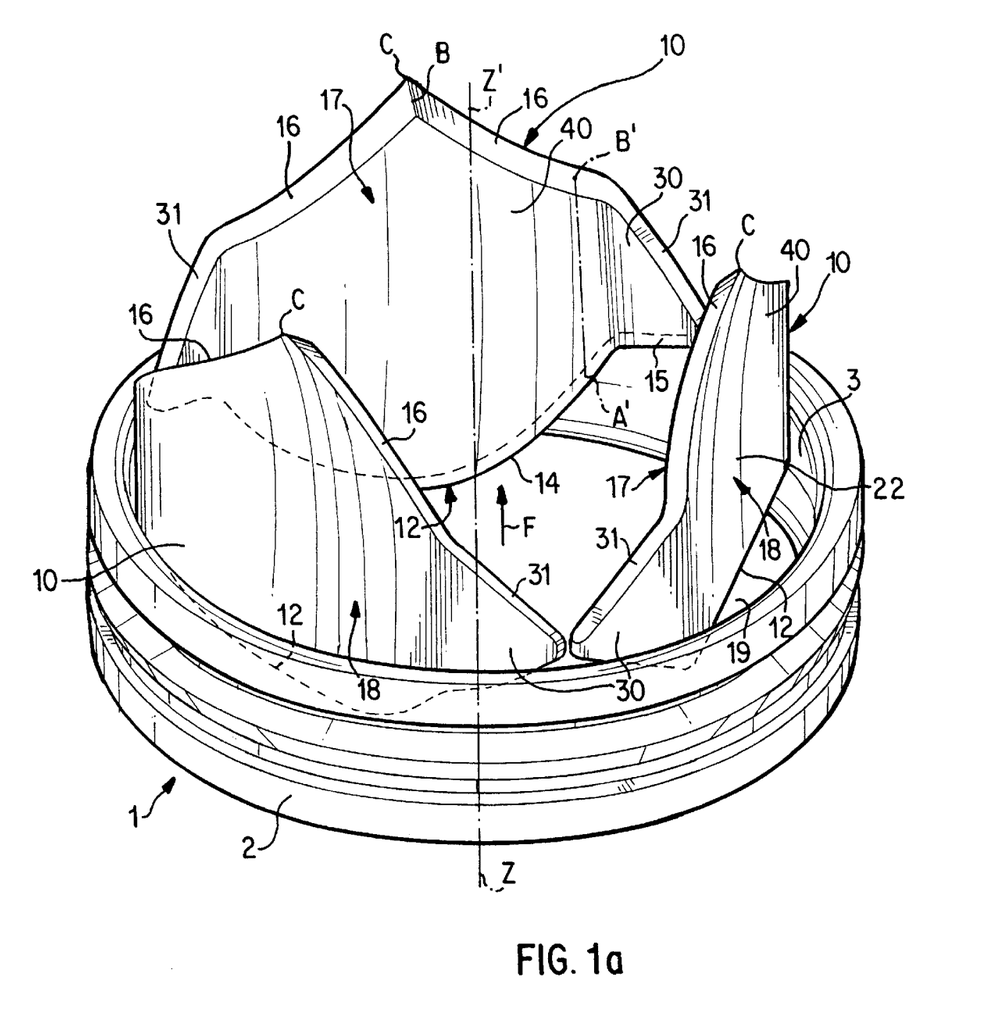
FIGS. 1a and 1b represent, respectively, a perspective view and a top view of a valve according to the invention in the open position.
Figure 1B:
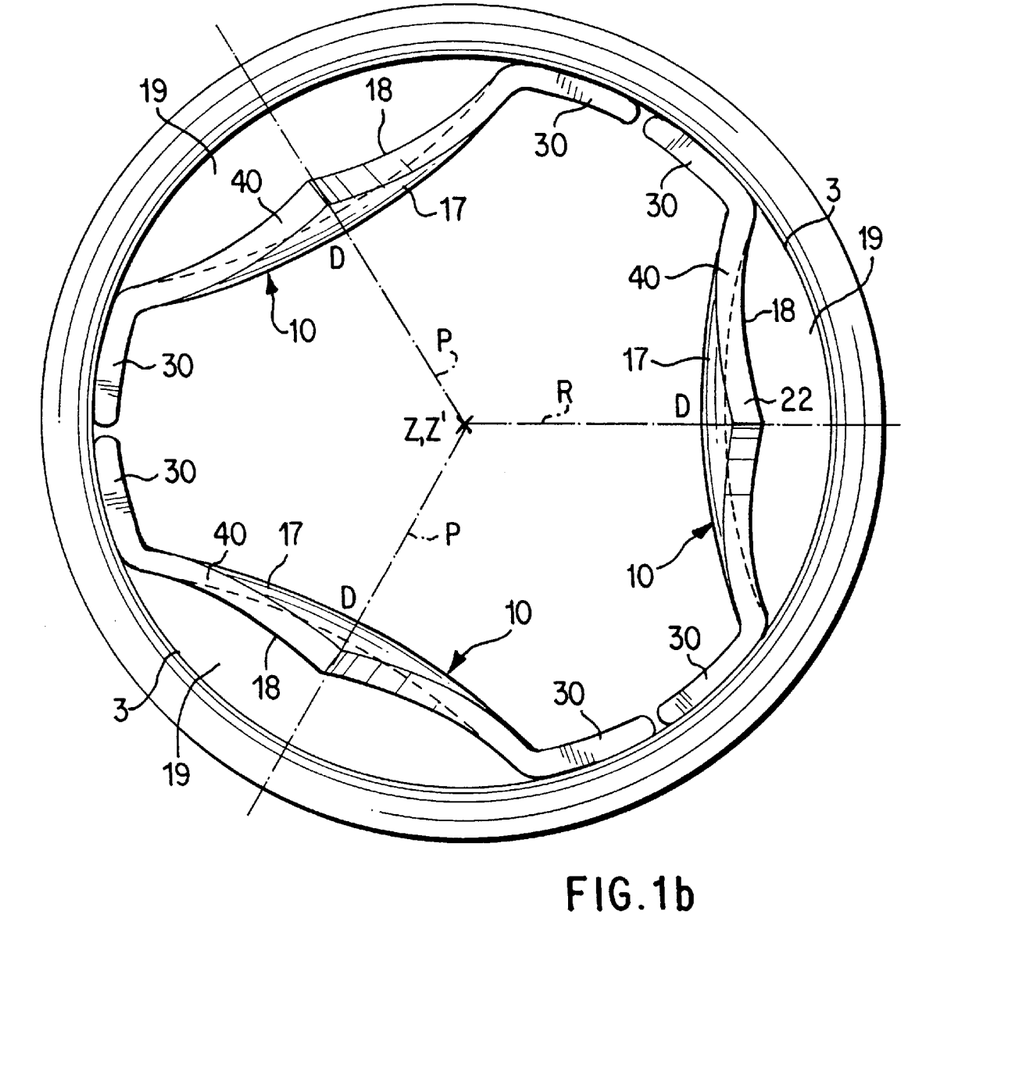
Figure 2:
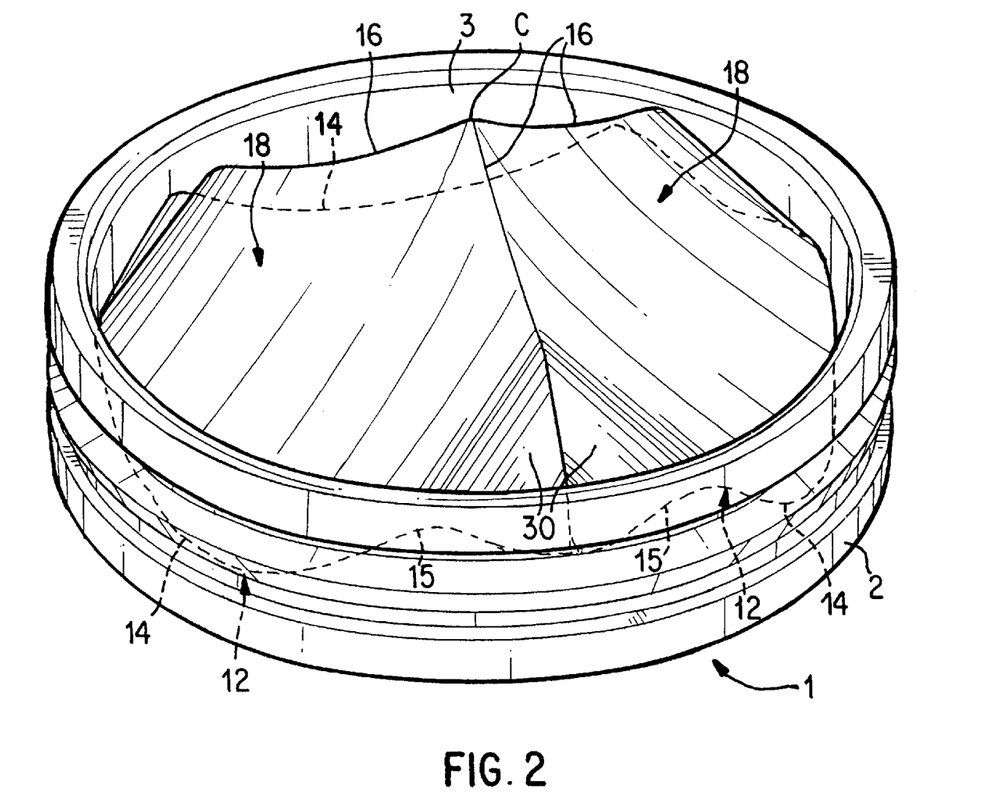
FIG. 2 represents the valve of FIGS. 1a and 1b in the closed position.
Figure 3:
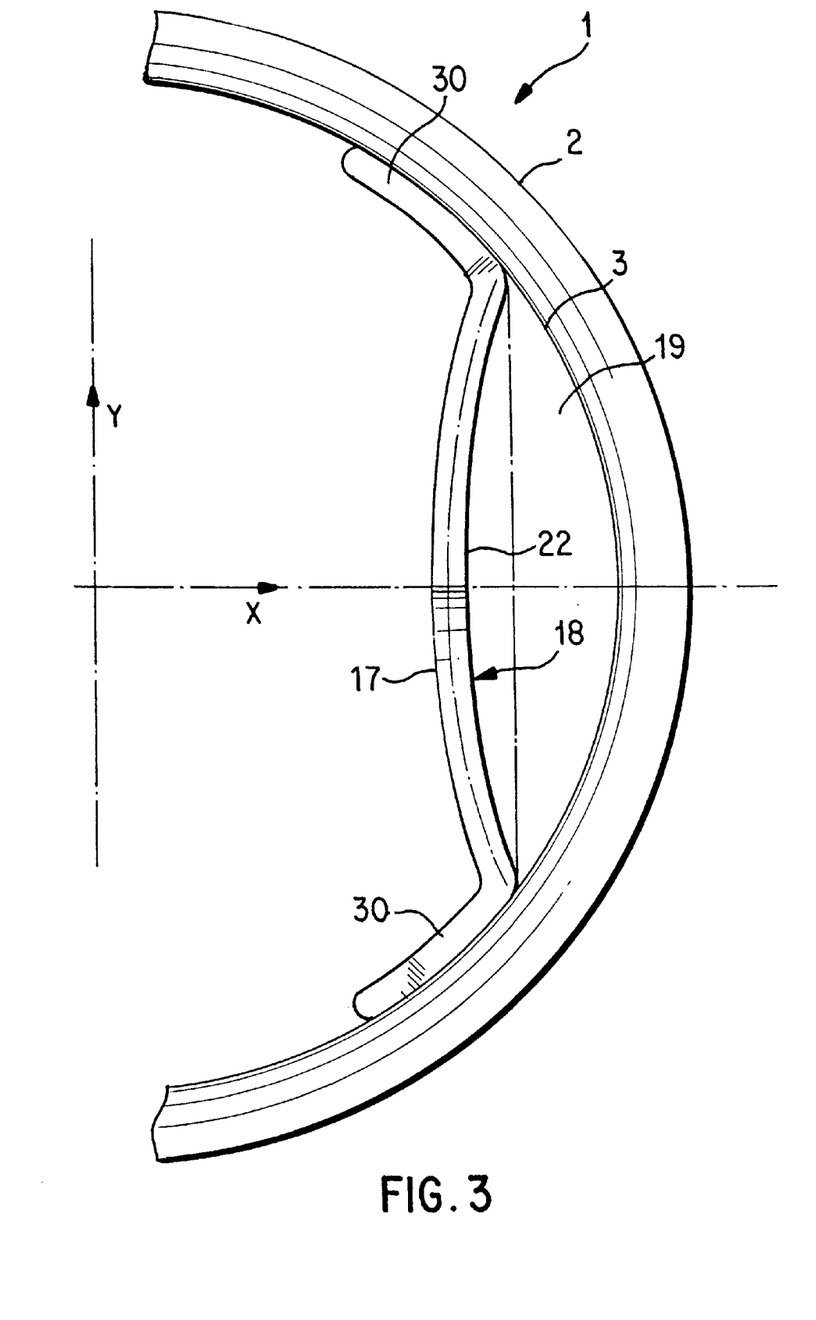
FIG. 3 represents a cross section of a leaflet in the open position, the section being through a plane perpendicular to the axis of the rim.

More specifically, in the open position, the region of each leaflet presents, in a section through a section plane containing the axis ZZ' of the rim 3 and, the point D closest to the axis of the rim, a profile having a maximum curvature $FL_M$ directed towards the axis ZZ' of the rim 3, which is between 1% and 20% of the length L of the leaflet defined as being the maximum distance between a median point A' of the leading edge 12 and a median point B' of the leading edge 16, in the cross section of the leaflet 10 which is parallel to the section plane when the leaflet is in the open position (FIG. 1a).

Figure 4:
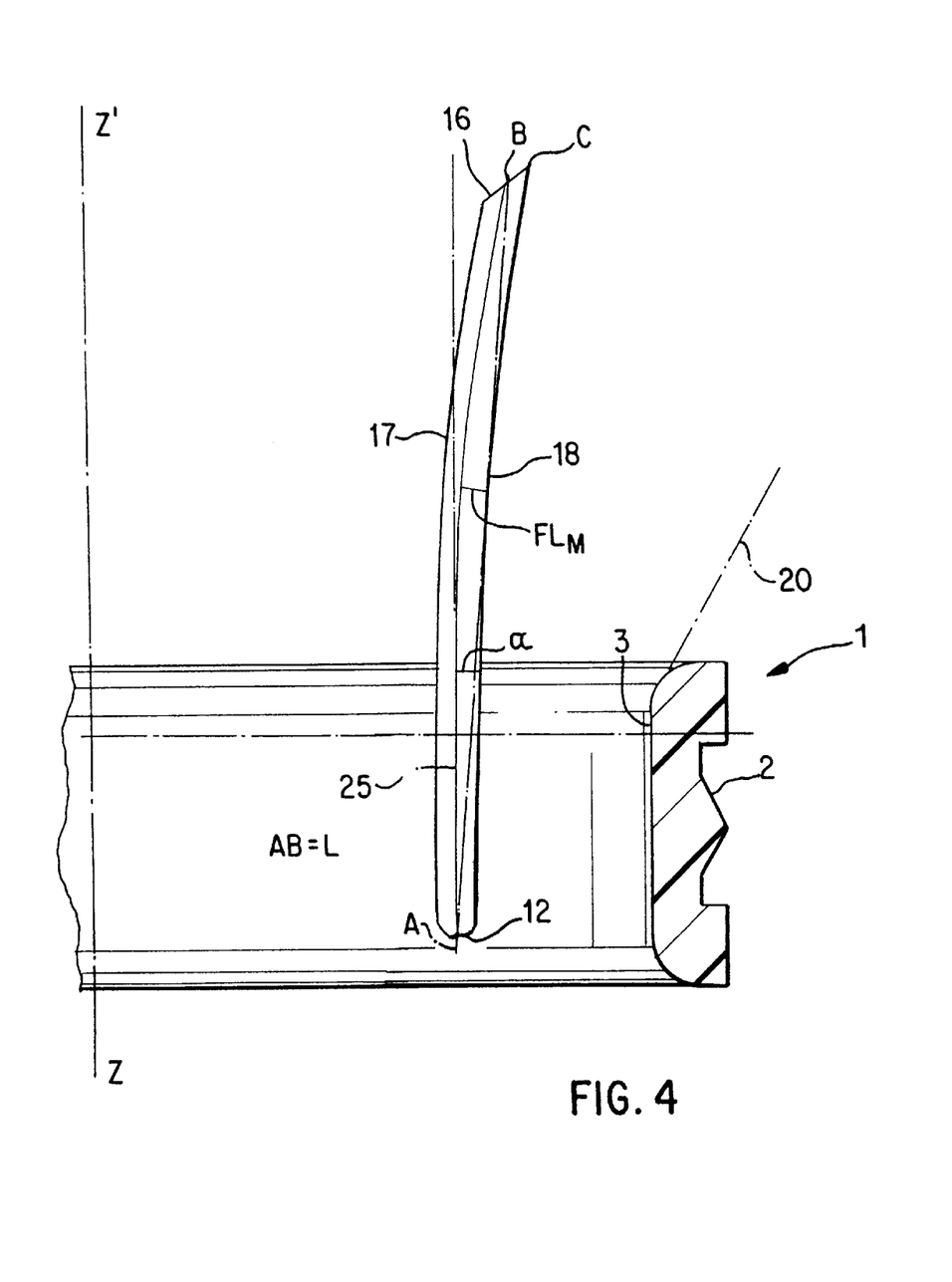
FIGS. 4 and 5 represent two variants of leaflets according to the invention, in the open position in cross section through a plane passing through the axis of the rim and point D of FIG. 1b.
Figure 5:
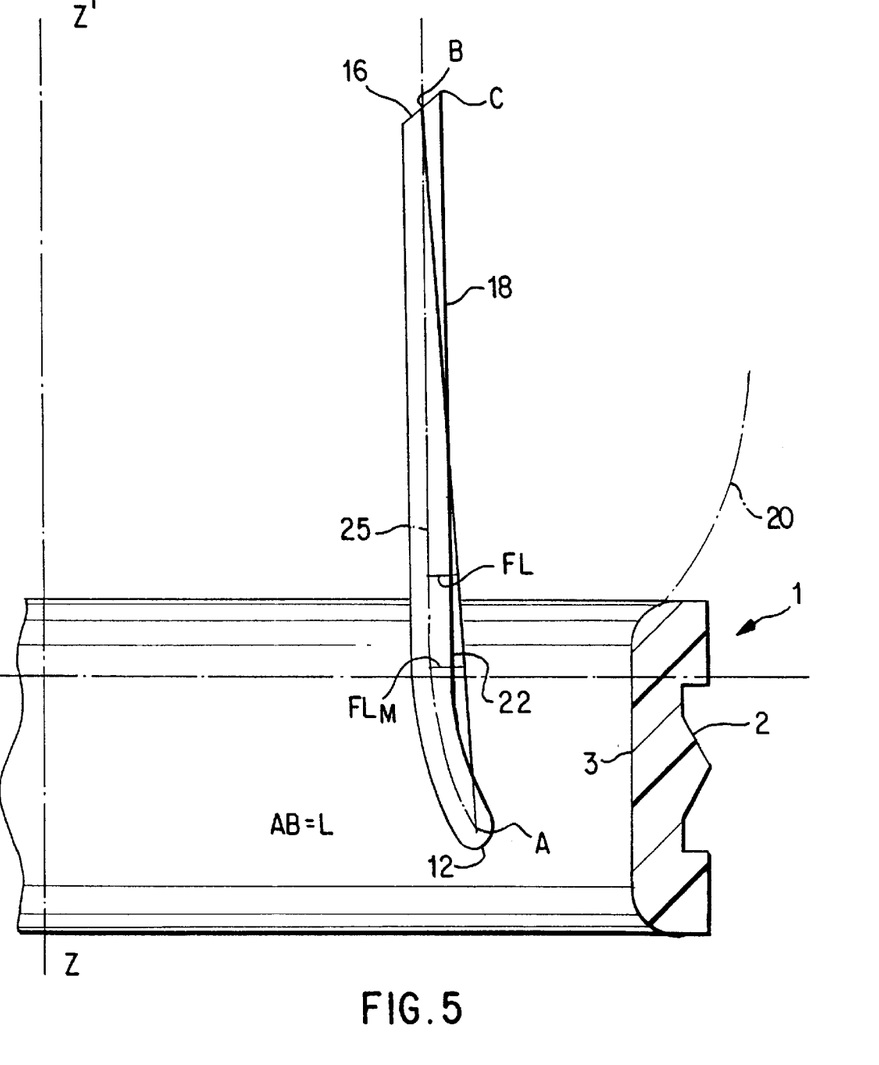

In addition, for each leaflet, in the open position, the line AB joining the ends of the section of the leaflet through said first plane forms, with the axis of the rim, an angle between $-10°$ and $+10°$ (FIGS. 4 and 5).

In general, the length L of the leaflet is the distance between the leading edge and the trailing edge in the section of the leaflet through the section plane.

The value of the curvature FL is defined as the distance between the profile and the line joining the ends of the section of the leaflet 10, that is the median point A' of the leading edge 12 and the median point B' of the trailing edge 16 through the above-mentioned section plane. More particularly, with reference to FIGS. 4 and 5, the curvature FL is defined as the distance between the line AB which joins the median point A of the leading edge 12 and the median point B of the trailing edge, and the median line 25 of the leaflet 10. The maximum curvature $FL_M$ is the maximum value of the curvature FL. The value of the maximum curvature $FL_M$ can be between 5% and 15%, preferably between 5% and 10%.

FIG. 4 illustrates a camber of the leaflet 10 which extends from the leading edge 12 to the trailing edge 16. FIG. 5 illustrates a camber of the leaflet 10 which is more accentuated in the vicinity of the leading edge 12 than in the vicinity of the trailing edge 16.

Satisfactory results can be obtained when one and/or the other value of the maximum curvature is between 1% and 5%, and more particularly between 3% and 5%, the shape of the leaflet in that case differing little from the flat shape which in itself is known.

If one wishes to optimize the results, one must take into account, notably if one of the above values exceeds 10%, the influence of the curvature on the opening of the leaflets and one the load loss of the direct blood flow, the selected value being then a compromise between the effectiveness during the opening of the leaflets and at the time when the leaflets are open (notably load loss), and the effectiveness at closing (closure volume).

A camber as defined above appreciably decreases the response time of the tilt of the leaflets and it promotes a rapid closing by holding, like the sails of a boat, the centripetal wall currents generated by the flow.

It should be noted that the invention applies only to mechanical cardiac valves with two or three leaflets, whose pivoting direction is physiological, that is, from the axis ZZ' of the rim 3 toward the rim 3 during the opening, and, as a corollary, from the rim 3 toward the axis ZZ' of the rim 3 during the closing.

It cannot be applied to bileaflet valves, whose pivoting direction is in the opposite direction, as is the case notably in the valve corresponding to U.S. Pat. No. 5,026,391 (PESKIN) where it appears in FIG. 13 that the direction of flow is in the direction of the arrow 20 and consequently the pivoting of the leaflets about the axes "P" occurs in the opposite direction. In the open position, the leaflets turn their concavity towards the rim, whereas in the closed position, because of the reversed pivoting direction with respect to the physiological direction, they turn their concavity towards the upstream region with respect to the direction of flow (arrow 20).

The specific optimal values of camber and eccentricity described in U.S. Pat. No. 5,026,391 are intrinsically connected to the pivoting direction of the leaflets with respect to the flow axis. In this configuration, the camber mentioned allows a decrease in the losses of charge and a reduction in the detachment zones during the opening phase (forward flow). During the valve closing, because of the reversed pivoting direction of the leaflets, the closing mechanism is entirely different.

U.S. Pat. No. 5,026,391 (Charles Peskin et al.) does not mention in the configuration that it proposes a negative effect of the concavity on the dynamic closure volume. In this reversed functional direction, compared to the physiological direction (outwardly closing leaflet), a concave curvature delays the tilting of the leaflets. The curvatures of leaflets shown in the Charles Peskin U.S. Pat. No. 5,026,391 in fact have a negative effect on the regurgitation rate. These curvatures cannot be opposite to the curvatures according to the present invention which favor exactly the opposite effect. The same objection can be made for U.S. Pat. No. 4,872,875 (Hwang).

The specific camber values which favor the natural closing mechanism therefore have an effective functional role only for the valves where the rotation of the leaflets occurs in the natural direction, such as those described notably in U.S. Pat. Nos. 4,120,299 and 5,123,918 (DASSAULT & LAPEYRE), and for which a zone of the leaflets turns its concavity toward the rim when the leaflets are in the open position and toward the downstream region with respect to the main flow direction of the blood flow when the leaflets are in the closed position.

The specific values are also different from those bileaflet valve described in U.S. Pat. Nos. 4,808,180 (JOHNSON, MEDTRONIC) and 4,676,789 (SORENSEN), where the pivoting direction of the leaflets is physiological, but the curvatures are reversed, of conical and convex type, because of their mechanical definition.

When the pivoting direction of the leaflets is physiological, a camber with concave shape exposed to the centripetal wall currents in the peripheral duct regions not only tends to increase the percentage of closing at the time when the flow becomes zero but also to decrease the time required to complete the closing. An adapted camber thus allows a reduction in the dynamic leakage volume. The concavity of the posterior side of the leaflets is preferably bidirectional: parallel to the flow axis on the vertical plane and perpendicularly to this axis on the horizontal plane, the leaflets being taken in the open position.

For the mitral version, and considering the leaflets 10 in the open position: the concavity parallel to the axis of the blood flow is advantageously of the ellipsoid type with a curvature located near the point C at ⅔ of the length L and the maximum amplitude which can reach 20% of the maximum length L of the leaflet. The radius of curvature which is tighter toward the point C allows the closing currents to have a more marked effect on the point C than on the base, thus favoring, as a result of a lever effect, the early tilting of the leaflets 10. This spatula-like shape also allows an appreciable increase in the surface area of coaptation of the three leaflets 10 between each other in the closed position, just like in the natural valve.

For the aortic version, and considering the leaflets 10 in the open position:

"The sail surface area" being smaller than in the mitral version because of the smaller size, the curvatures of the leaflets 10 are advantageously more marked.

The cambers so defined tend to match the shape of the vortex generated by the flow in the aortic sinuses and in the ventricular cavity and they tend to ensure a good sweeping of the entire downstream side 18 of the leaflets 10 as well as that of their guidance tracks on the three solid parts of the orifice. In addition, this curvature tends to orient the blood column which flows back towards the internal wall of the orifice of the valve in a direction which is not parallel to the flow axis, which can reduce the shearing forces to which the blood is exposed as it passes through the interstices (see studies of static leakage by CFD).

In contrast to all the known mechanical cardiac valves, the leaflets 10 of the mechanical valve which is the object of the present invention also present considerably different curvatures in the mitral version and in the aortic version.

Although the shearing forces are much larger during the static leakage than during direct flow, the reflux flow is much less than the [direct] flow output. It is not yet known precisely what the respective contributions of the two phases of flow in the destruction of red blood cells and platelets are, and in the thrombogenicity.

Ongoing (unpublished) studies performed on artificial hearts have, however, shown that the contribution of the reflux is not negligible and that this contribution is not the same in the aortic position as in the mitral position. The critical hemolysis factor for the reflux is less the leakage flow alone but rather its turbulent or laminar character which depends on the pressure regimen (diastolic or systolic) and also on the gap width.

In vitro studies (unpublished) performed with an artificial heart equipped with 29-mm valves of the Bjork type have shown that a constant pressure regimen (diastolic) results in a doubling of the leakage flow when the gap is broadened from $5/100$ mm to $1/10$ mm. The hemolysis rate is little modified by the increase in the leakage flow. Conversely, in the pulsed pressure regimen (systolic), the hemolysis considerably increases as soon as the variation in pressure as a function of time dP/dT exceeds 2000 mm Hg/sec. The smaller the gap, the higher are the speeds, the greater the shearing rate and the higher the hemolytic potential. The hemolysis rate decreases if one broadens the gap by a sufficient value in spite of the concomitant increase in the leakage flow. The hemolytic potential of the leakage is much greater in the mitral position than in the aortic position.

Other experimental observations seem to indicate that a laminary type leakage is much less traumatic than a turbulent type leakage. The optimal gap width is thus the function of the duration and pressure conditions of the leakage, and it is not the same for the aortic versions and for the mitral versions.

On the aortic level, the diastolic leakage occurs at a constant pressure of approximately 80 mm Hg for a duration on the order of 450 msec. The static leakage of a standard bileaflet valve of size 23 is 300 mL/min for a mean gap width of 4/100 mm. The gap width is less critical in its effect on the hemolysis rate than for the mitral valve. The shearing forces on the blood during an aortic leakage would be rather of the laminary type.

On the mitral level, the systolic leakage occurs at the pulse pressure of 0–160 mm Hg for a duration of typically 300 msec and with a higher dP/dT (1500, 3000 and 4500 mm Hg/sec for 70, 90 and 120 cycles per min, respectively). The static leakage of a standard bileaflet valve the size 29 is on the order of 230 mL/min for an interstice whose mean width is less than 4/100 mm. Starting with a certain critical value, the increase in the gap width decreases the hemolysis rate. The shearing forces on the blood during a mitral leakage would be rather of the turbulent type.

Clinical observations (Gerson Rosenberg, personal communication, University of Pennsylvania) made on patients with artificial heart confirm these experimental data: the hemolysis generated by the valves located in the mitral position is greater than the hemolysis generated by the valves located in the aortic position. In the mitral position, the hemolysis rate is greater the smaller the gap width and the higher the variation in pressure as a function of time dP/dT. It has happened that an artificial heart had to be replaced because of a high degree of hemolysis. The simple replacement of the mitral valves by valves of the same type which are less sealing was capable of producing a spectacular correction of the blood cell destruction.

The designers of cardiac valves have not yet taken this phenomenon into account. The same valves are used, regardless of whether the valves to be replaced are aortic or mitral. The designers have been obligated to limit the static leakage by reducing the gap width to maintain the overall leakage rate at an acceptable level.

"Peripheral jets" having a length of more than 1 cm around the closed leaflets of the valves marketed by the company St. Jude Medical are observed in the mitral position in all the patients during echo-Doppler examinations. They form characteristic shower head images. The manufacturers of bileaflet valve attribute these "jets" to a controlled rinsing function of the joint areas, which reduces the risk of coagulation at this level and thus the catastrophic blockage of the leaflets. Given the configuration of the articulations, these "rinsing jets" are very useful and they explain the low rate of thrombosis observed with these valves.

Although the number of passages of cells increases when the gap between the components is larger, the traumatic effect on red blood cells and on platelets decreases when the gap is less narrow. For the same pressure regimen, an increase in the gap width corresponds to increases in the leakage flow and decreases in the speed of the peripheral jets and the shearing rate. A very narrow gap can have a very traumatic effect and require the replacement of the valve.

To reduce the hemolysis rate at the level of the mitral static leakage, one must therefore completely eliminate the gap (<2/100 mm) which eliminates the rinsing function, or one must sufficiently enlarge the gap to return the shearing forces to a level comparable to that of the aortic valves. For the mitral valves, the optimal values of the gap under physiological flow, pressure and dP/dT conditions are equal to or larger than approximately 0.8–1/10 mm. Such a large gap is only functionally acceptable if the closure volume is decreased, because otherwise the corresponding total leakage would be entirely prohibitory.

Although there is still no scientifically proven relation between the degree of hemolysis and the thrombogenicity of the cardiac valves, clinical experience suggests that the reduction in the shearing forces can decrease the thrombolytic complications by reducing the state of reactive hypercoagulability which accompanies any blood cell destruction (Renate Koppensteiner et al.: Blood rheology after cardiac replacement with mechanical prostheses or bioprostheses. The American Journal of Cardiology, January 1, 1991, pp. 79–83): the tissue valves, which are known to have a low thrombogenicity, do not cause hemolysis; mitral prostheses are known to be more thrombogenic than aortic prostheses.

At the time of the closing of the mechanical valve of the conventional type in the mitral position, the impact of the leaflets on the opening generates a pressure gradient on the order of 750 mm Hg during the time (approximately 1 msec) after the closing. The instantaneous leakage flow generates shearing forces on the edges which greatly exceed the lethal threshold for red blood cells and platelets (Lee and Chandran, Valve Medtronic-Hall valve of size 29 with a gap of 0.05 mm: Wall Shear Stress=1500 and 2500 Pa: Reynolds number=100–50 for dP/dT of 750 mm Hg/sec and 3000 mm Hg/sec, respectively). If one decreases the instantaneous pressure gradient at the impact by reproducing the closing mechanism of natural valves, the shearing forces are decreased, and the risk of cavitation is eliminated. In addition, it is possible to specifically adapt the optimal value of the gap for each one of the two configurations, aortic and mitral.

In the mitral position, the closure volume is relatively larger than the static leakage volume. A significant decrease in the closure volume thus permits an appreciably larger gap width. Conversely, in the aortic position, the dynamic closure volume is relatively speaking smaller than the static leakage. One can advantageously reduce the gap width and decrease the static flow.

For aortic versions of the cardiac valve, which is the object of the present invention, the gap width is preferably regulated so as to permit, at a constant pressure of 100 mm Hg, a leakage flow on the order of 0.5 L/min, regardless of size. This value corresponds to a nominal leakage of 2–3% of the systolic volume in the physiological frequency, pressure and flow regimen. The total regurgitation rate is then appreciably less than that of the known mechanical prostheses. The mean gap width is typically on the order of 2/100 mm.

For the mitral versions of the cardiac valve, which is the object of the present invention, the gap width is preferably regulated so as to allow, at a constant pressure of 100 mm Hg, a leakage flow on the order of 0.8 L/min, regardless of the size. This value corresponds to a nominal leakage of 7–8% of the systolic volume in a physiological frequency flow and pressure regimen. The total regurgitation rate is identical to or slightly larger than that of the known mechanical prostheses. The gap width is at least 4 times larger than the gap width of the aortic valves, or, typically, 0.8–1/10 mm.

In contrast to all the known mechanical valve prostheses which have a gap between the components having an identical width for the aortic versions and the mitral versions, the optimized valve, which is the object of the present invention, has a gap width which is larger in the mitral position than in the aortic position.

The specific means which allow improving the closing mechanism during the phase of the flow deceleration and thus decreasing the dynamic closure volume accordingly, according to the present invention, impart critical advantages to a mechanical valve:

1. On the functional level: reduction of dysfunction in low output and high frequency regimens by decreasing the regurgitation. 2. At the structural level: increase in the cavitation threshold, better wear resistance, reduced acoustical production. 3. At the biological level: possibility, in some cases, of providing a much larger space between the opening of the valve and its closure elements in the mitral configuration, which ensures a better rinsing of the opening, a reduction of its hemolytic potential and a decrease of the thrombogenicity.

Mitral valves are larger than aortic valves. The standard size for mitral valves is 29 mm. The standard size for aortic valves is 23 mm. The "compulsory" closure volume is naturally much larger for mitral valves. Consequently, it is advantageous to reduce the closure volume above all for the mitral configuration.

Because of their antinatural "countercurrent" direction of tilt, the classic monodisk valves or the bileaflet valves close only due to the reflux, at the time of the reversal of the output, at the very beginning of the diastole in the aortic position and at the very beginning of the systole in the mitral position. The closure caused by the deceleration of the output is zero, whereas it is almost 90% with natural valves. The reflux volume is large, and the closure speed is very high.

According to the invention, where the closing of the leaflets, on the contrary, occurs in the physiological direction, the wall currents generated by the filling of the ventricle or of the sinuses exert a lateral force on the leaflets 10 which return their tip C in the axis direction of the blood output. The leaflets 10 then start their closing prematurely, as soon as the flow through the opening decreases. The closing speed is less high. The compulsory closure volume is smaller, and the time required to complete the closing is shorter, so that the dynamic reflux volume is smaller.

It has been experimentally demonstrated that the closer the tilt axis 11 of the leaflets 10 is to the edges of the opening, the greater the lever effect on the leaflets and the less large a force is required for the closing. The leaflets 10 are thus particularly sensitive to the closing currents if the tilt axis is more off center. The degree of eccentricity moves in the same direction as the closing angle: the larger it is, the smaller the volume regurgitated at closing.

U.S. Patent No. 4,820,299 (DASSAULT-LAPEYRE) describes a valve having a tilt axis located perpendicularly at a distance of at least 75% of the values of the internal radius R of the opening. This value is appropriate for the aortic definition since the aortic valves are smaller and since the compulsory closure volume is relatively speaking smaller.

However, it is especially advantageous for the mitral definition to appreciably increase the eccentricity by bringing the tilt axis of the edges of the opening of the valve up to a distance of 80–84% of the radius R.

What is claimed is:

1. A mechanical valve prosthesis device comprising:

a base having an external portion forming a suture ring and an internal portion forming a rim in which blood flow moves along in a main flow direction parallel to an axis of the rim;

at least two closing leaflets movable between a closed position and an open position, each of the at least two closing leaflets having a tilt axis and having a leading edge in contact with the rim and a trailing edge in contact with the adjacent trailing edge of the adjacent leaflet when the at least two closing leaflets are in the closed position, each of the at least two closing leaflets having an outer surface with a region that is concave in every direction along the outer surface.

2. The mechanical valve prosthesis device according to claim 1 wherein, the rim has a center axis, a portion of the outer surface of the at least two closing leaflets has a concave surface, and in the open position, the concave portion of each of the at least two closing leaflets being closest to the center axis, wherein the outer surface portion has a curvature between 1% and 20% of a length L of the leaflet defined as being the maximum distance between the leading edge and the trailing edge and wherein an angle between −10° and +10° is formed between each of the at least two closing leaflets and an adjacent section of the rim.

3. The device according to claim 2, wherein at least one of a first and second maximum curvatures is between 5% and 15%.

4. The device according to claim 3, wherein at least one of the first and second maximum curvatures is between 5% and 10%.

5. The device according to claim 3, wherein at least one of the first and second maximum curvatures is between 10% and 15%.

6. The device according to claim 2, wherein at least one of the first and second maximum curvatures is between 1% and 5%, and more particularly between 3% and 5%.

7. The device according to claim 2, wherein at least one of the first and second maximum curvatures is between 15% and 20%.

8. The device according to claim 2, wherein a first plane is the plane of symmetry of the corresponding leaflet.

9. The device according to claim 2, wherein in the closed position, a mean value of an interstice between the leading edges of the at least two closing leaflets and the rim and an interstice between the trailing edges is between 40 and 100 $\mu$m.

10. The device according to claim 9, forming a mitral valve.

11. The device according to claim 1 wherein each one of the leaflets has a tilt axis located at a distance equal to at least 75% of the radius of the internal portion.

12. The device according to claim 11 characterized in that wherein the distance is between 80% and 85% of the radius.

13. The device according to claim 1, wherein the outer surface of each of the at least two leaflets faces the rim when the leaflets are in an open position.

14. The device according to claim 1, wherein the concave surfaces of each of the at least two closing leaflets are symmetrically opposed.

15. The device according to claim 1, further comprising a duct region, the duct region formed between the rim and the outer surface of each of the at least two leaflets when the at least two leaflets are in the open position.

* * * * *